United States Patent
Griffith et al.

(10) Patent No.: US 12,357,320 B2
(45) Date of Patent: Jul. 15, 2025

(54) TOURNIQUET

(71) Applicants:Benjamin Latham Griffith, Salt Lake City, UT (US); Arrius Lee Sorbonne, Salt Lake City, UT (US)

(72) Inventors: Benjamin Latham Griffith, Salt Lake City, UT (US); Arrius Lee Sorbonne, Salt Lake City, UT (US)

( * ) Notice: Subject to any disclaimer, the term of this patent is extended or adjusted under 35 U.S.C. 154(b) by 264 days.

(21) Appl. No.: 17/937,349

(22) Filed: Sep. 30, 2022

(65) Prior Publication Data

US 2023/0165591 A1    Jun. 1, 2023

Related U.S. Application Data

(60) Provisional application No. 63/250,828, filed on Sep. 30, 2021.

(51) Int. Cl.
*A61B 17/132* (2006.01)
*A61B 90/30* (2016.01)

(52) U.S. Cl.
CPC .... *A61B 17/1327* (2013.01); *A61B 2090/304* (2016.02)

(58) Field of Classification Search
CPC .............. A61B 17/132; A61B 17/1322; A61B 17/1325; A61B 17/1327; A61B 17/135; A61B 17/1355; A61B 5/022; A61B 5/02208; A61B 5/02216; A61B 5/02225; A61B 5/02233; A61B 5/022441; A61B 5/0225; A61B 5/02255; A61B 5/023; A61B 5/0235
See application file for complete search history.

(56) References Cited

U.S. PATENT DOCUMENTS

| | | |
|---|---|---|
| 5,607,448 A | 3/1997 | Stahl et al. |
| 7,776,064 B2 | 8/2010 | Jennifer et al. |
| 7,842,067 B2 | 11/2010 | Esposito |
| 7,892,253 B2 | 2/2011 | Esposito et al. |
| 7,981,135 B2 | 7/2011 | Thorpe |
| D649,642 S | 11/2011 | Johnson |
| 8,047,850 B2 * | 11/2011 | Esposito ................ G09B 23/28 434/262 |
| 8,303,620 B2 | 11/2012 | Johnson et al. |
| 8,343,182 B2 | 1/2013 | Kirkham |
| 8,348,970 B2 | 1/2013 | Janota |
| 8,888,807 B2 | 11/2014 | Esposito |
| 8,926,651 B2 | 1/2015 | McDonald et al. |

(Continued)

FOREIGN PATENT DOCUMENTS

WO      2020227697 A1    11/2020

*Primary Examiner* — Kathleen S Holwerda
(74) *Attorney, Agent, or Firm* — Lightfoot & Alford PLLC

(57) ABSTRACT

A tourniquet includes a support structure with a slot at one end for receiving a strap and a gate opposite the at least one strap slot for retaining a windlass relative to the support structure. A first end of the strap is threaded through the windlass and the slot and is attached back upon itself to form a loop. The second free end of the strap is configured to wrap around an extremity, through the slot and secured back to itself. Winding the windlass relative to the support structure causes the strap to twist between the windlass and the support structure to tighten the strap around the extremity. One end of the windlass can then be inserted through the gate to hold the windlass relative to the support structure.

12 Claims, 14 Drawing Sheets

(56) References Cited

U.S. PATENT DOCUMENTS

| | | |
|---|---|---|
| D739,027 S | 9/2015 | Johnson et al. |
| 9,492,177 B2 | 11/2016 | Saunders et al. |
| 10,016,203 B2 | 7/2018 | Esposito |
| 10,258,347 B2 | 4/2019 | Hopman et al. |
| 10,278,708 B2 | 5/2019 | Demas et al. |
| 10,363,046 B2 | 7/2019 | Hopman et al. |
| 10,568,636 B2 | 2/2020 | Demas et al. |
| 10,765,437 B1 | 9/2020 | Antonio |
| 2007/0005107 A1 | 1/2007 | Janota |
| 2008/0243172 A1 | 10/2008 | Thorpe |
| 2010/0057120 A1 | 3/2010 | Kirkham |
| 2012/0071917 A1* | 3/2012 | McDonald ............. G01L 5/102 116/212 |
| 2013/0267994 A1 | 10/2013 | Crowder et al. |
| 2016/0135575 A1 | 5/2016 | Solomon et al. |
| 2018/0042616 A1 | 2/2018 | Demas et al. |
| 2018/0168663 A1 | 6/2018 | Hill |
| 2018/0228497 A1 | 8/2018 | Dimino et al. |
| 2020/0015828 A1 | 1/2020 | Johnson et al. |
| 2020/0367909 A1 | 11/2020 | Rankins et al. |
| 2021/0000482 A1 | 1/2021 | Parsons |
| 2021/0137531 A1 | 5/2021 | Rivero |
| 2021/0153873 A1 | 5/2021 | Peterson et al. |

\* cited by examiner

TOURNIQUET

CROSS-REFERENCE TO RELATED APPLICATION

This application claims priority to U.S. Provisional Patent Application Ser. No. 63/250,828 filed on Sep. 30, 2021, with the United States Patent and Trademark Office, the entirety of which is incorporated by this reference.

BACKGROUND OF THE INVENTION

Field of the Invention

The invention relates generally to tourniquets and more specifically to tourniquets with windlass mechanisms for tightening the tourniquet.

Description of the Related Art

For centuries, when severe injury occurs to an extremity, such as a leg or arm, tourniquets have been used in the field to apply pressure to the injured extremity above the injury and to constrict blood loss through the injured extremity until medical personnel can treat the injured person. The severity of the injury depends on the location and path of the injury and whether vascular components have been compromised such that the person is losing a life threatening amount of blood.

In particular, when a major artery has been severed, blood loss is rapid and controlling the blood loss not only becomes critical, but the time in which the blood loss is controlled can be critical to the survival of the injured person. Quick and proper application of a tourniquet proximate the vascular disruption can be the difference in the survival of the injured persons. However, for a tourniquet to be effective in controlling blood loss, it must first be properly applied and secondly must remain in place with consistent pressure applied.

Despite many advances in the design and use of tourniquets, there still exist limitations in the effectiveness of various implementations, particularly in the context of rapid and reliable application of the tourniquet in conditions that may typically be found on the battlefield or in other emergency situations. For example, the device used to maintain the tourniquet in a tensioned state, such as a windlass, may be suspectable to being disengaged and allow the pressure being applied to be reduced to the point where blood flow through the injury recurs. In addition, once a tourniquet has been applied to a person, emergency personnel arriving on scene may not immediately notice that a tourniquet has been applied, which if left unattended could cause further damage to the extremity below the placement of the tourniquet. Furthermore, some tourniquets are not particularly useful in application to smaller extremities such as people with small wrists or to fingers.

Thus, there exist a need in the art for an improved tourniquet that is easily applied with one hand by the injured person, is easily identifiable when applied, remains secure to the extremity once applied and can be used on smaller extremities to effectively stop bleeding.

SUMMARY OF THE INVENTION

The invention provides various embodiments of tourniquets having a strap connected to a tensioning device that can be maintained in place once tension has been applied to the strap to effectively stop a loss of blood through an injured body extremity.

In one embodiment, the tourniquet may be configured to allow application by the injured person or by a third person with a single hand. A tensioning mechanism coupled to a tourniquet strap allow the tourniquet strap to be tightened. Once sufficiently tightened, the tensioning mechanism can be locked in position.

In one embodiment, a self-illuminating visual indicator is provided on the tourniquet that can be activated when the tourniquet is applied to an extremity.

The tourniquet of the present invention includes several significant improvements over the prior art. Specifically, the tourniquet of the present invention has a 50-60% reduction in size over similar prior art devices thereby increasing options to carry the tourniquet on a person, such as in a pants or shirt pocket or in other places. In addition, the smaller size of the tourniquet of the present invention allows for more than one such tourniquet to be more easily carried by a person as more than one tourniquet may often be needed, even for the same injury.

The tourniquet of the present invention also includes various improved features such as the gate, illuminating feature, instructions for use on the device, and hooked windlass allow for improved ease of use, especially in extreme stress conditions when a person or animal is bleeding out.

The tourniquet of the present invention also includes significantly improved reliability over the prior art. Specifically, the gate lock and hooking features of the windlass ensure that windlass cannot be accidentally or inadvertently released, a condition that could easily lead to death.

The tourniquet of the present invention is also configured to be usable on small limbs. Many prior art tourniquets cannot be used properly on small limbs, such as small wrists, on children, or on pets or K9s. The tourniquet of the present invention is configured to be useful on large limbs, such as the upper thigh of a person, as well as on limbs as small as 1 inch in diameter, which is not possible by many other prior art tourniquets.

The ability for the tourniquet of the present invention to be illuminated, either by self-illumination when applied or by user operation is also a significant improvement over the prior art. The incorporation of a glow stick into the tourniquet of the present invention provides some localized light at the tourniquet for users to see by and ensure proper use and securing of the tourniquet. incorporation of a glow stick into the tourniquet of the present invention also ensures that the tourniquet will be immediately seen by first responders and make it more likely for a person with the illuminated tourniquet to be found by others even after losing consciousness.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in, and constitute a part of this specification; illustrate embodiments of the invention and together with the detailed description serve to explain the principles of the invention. No attempt is made to show structural details of the invention in more detail than may be necessary for a fundamental understanding of the invention and various ways in which it may be practiced. For the purpose of illustrating the invention, there is shown in the drawings exemplary embodiments which illustrate what is currently considered to be the best mode for carrying out the invention, it being understood, however, that the invention is not limited to the specific instruments disclosed. In the drawings.

DETAILED DESCRIPTION OF THE INVENTION

Figure 1:
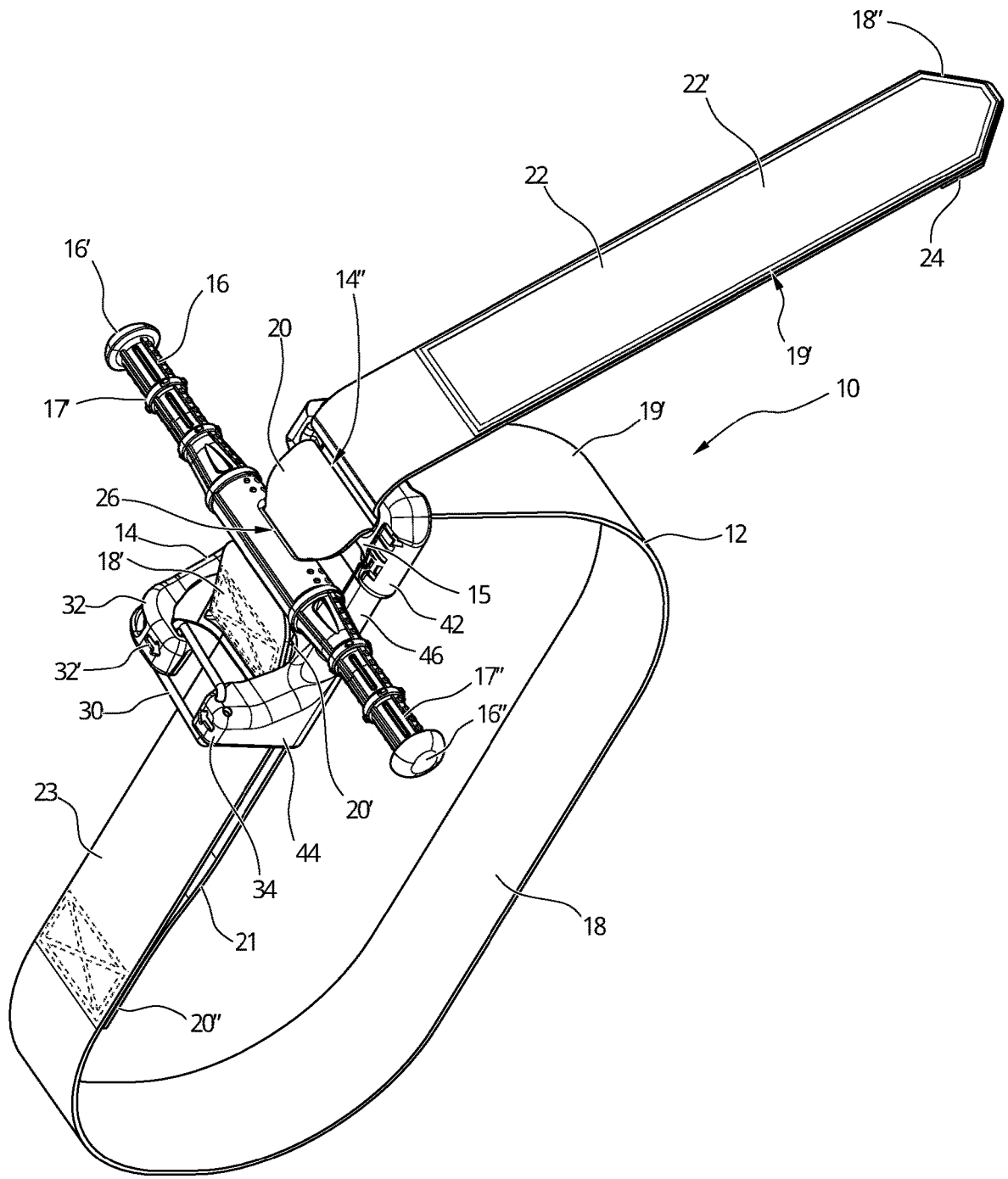
FIG. 1 is top perspective view of a first embodiment of a tourniquet in accordance with the principals of the present invention.

It is understood that the invention is not limited to the particular structures, etc., described herein, as these may vary as the skilled artisan will recognize. It is also to be understood that the terminology used herein is used for the purpose of describing particular embodiments only and is not intended to limit the scope of the invention. It also is to be noted that as used herein and in the appended claims, the singular forms "a," "an," and "the" include the plural reference unless the context clearly dictates otherwise. Thus, for example, a reference to "a strap" is a reference to one or more straps and equivalents thereof known to those skilled in the art.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32 etc., are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Moreover, provided immediately below is a "Definition" section, where certain terms related to the invention are defined specifically. Particular devices and materials are described, although any methods and materials similar or equivalent to those described herein can be used in the practice or testing of the invention. All references referred to herein are incorporated by reference herein in their entirety.

The term "vertically" as used herein generally refer to upward and downward directions when observing components, e.g., buckles, etc. from a side view.

The terms "laterally", "transversely" or "horizontally" as used herein generally refer to directions substantially perpendicular to the vertical direction when observing components, e.g., buckles, etc. from a side view.

Figure 2:
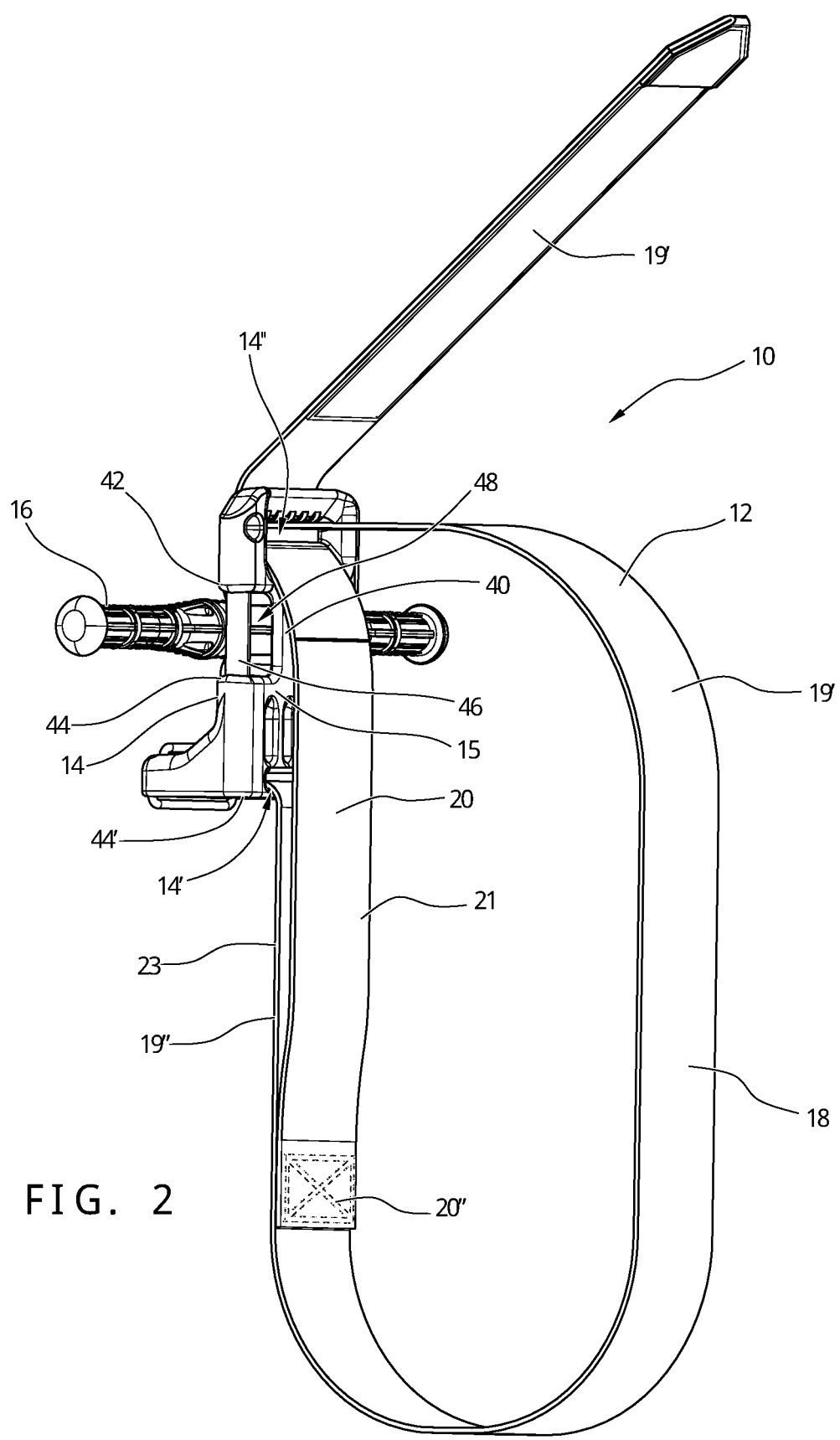
FIG. 2 is a bottom perspective view of the tourniquet shown in FIG. 1.

FIGS. 1 and 2 illustrate a tourniquet, generally indicated at 10, in accordance with the present invention. The tourniquet 10 is comprised of three structures or assemblies including a strap 12, a strap securing structure 14 having a base 15 in the form of a slide buckle, and a tensioning device 16 in the form of a windlass. The strap 12 is comprised of a plurality of strap portions 18, 20, 22 and 24 that may be formed from a single strap or separate strap sections that are sewn together or otherwise permanently attached to one another. Strap member 18 is comprised of a length of a flexible but non-stretchable strap material (such as nylon webbing) with mixed hook and loop fastener on one side 19' of the strap material so that the side 19' can be affixed to itself when the side 19' is overlapped upon itself. Hook and loop mixed tape is comprised of a length of webbing material in the form of a strap that is not significantly stretchable in a lengthwise direction and that has both hooks and loops woven together on the same side of the webbing material with the side with hooks and loops capable of being releasably attachable to itself with the hooks and loops of one portion attaching to the loops and hooks, respectively, of an opposing overlapping portion. A first end 18' of the first strap portion 18 extends through a first transverse slot 14' in the securing structure 14 and is fixedly attached to a first end 20' of the strap portion 20. The strap portion 20 passes through a longitudinally extending, transverse slot 26 in the windlass 16 and through a second transverse slot 14" in the opposite end of the securing structure 14. The windlass 16 as shown in FIG. 1 is an unwound state and is oriented transverse to the strap member 20. The strap portion 20 extends from proximate the second transverse slot 14", under the securing structure 14 and back along the under side 19" of the strap portion 18. The second end 20" of the strap portion 20 is fixedly attached to the inside of the strap portion 18 a distance, such as between about 1-4 inches or more, from the first slot 14' of the securing structure 14 so as to form a loop 21 between the strap portion 18 and the strap portion 20. The loop 21 thus extends from the slot 14" to the second end 20" of the strap portion 20 and extends under the securing structure 14 on a bottom side thereof and through the slot 26 in the windlass 16, over the top of the securing structure 14 and through the first slot 14' in the securing structure 14 and to the second end 20" where it is attached to the other end to complete the loop 21. As will be described in more detail, the strap portion 23 extending from the windlass 16 to the second end 20" is retracted by the windless 16 as the windless 16 is wound relative to the securing structure 14 when tightening the strap 12 around an appendage of a person or animal in need of the tourniquet 10. That is, as the windless 16 is wound or rotated relative to the support structure 14, the strap portion 23 between the slot 14' and second end 20" is pulled through the slot 14' thereby tightening the strap portion 18 so long as the strap portion 22 has been secured to strap portion 18 with the hook and loop material on side 19'. When the strap portion 18 has been sufficiently tightened around an appendage (arm, leg, finger, paw, etc.) of a person or animal, one end of the windlass 16 can be secured within the gate member 30 to maintain the tension on the strap portion 18.

The securing structure 14 comprises the base 15 in the form of a generally rectangular platform 40 (see FIG. 2) generally in the form of a plate, a biased gate member 30 at one side that is held between distal ends of arms 32 and 34 outwardly depending from the platform 40. The gate member 30 is comprised of a bent metal rod outlining a generally rounded rectangular shape. The gate member 30 has first and second ends each pivotally attached to opposite sides of the distal end of the arm 34 with the first and second ends horizontally offset from one another with the first end positioned closer to the arm 32 and the second end positioned farther from the arm 32 than the first end. This offset arrangement creates a biasing force on the gate when the gate is moved toward the platform 40 of the outwardly depending so that the gate is biased into engagement with the hook portion 32' of the arm 32 away from the platform 40. The gate member 30 may also be comprised of plastic or other materials known in the art, but is generally configured to be biased into a closed position so as to retain the windlass 16 when inserted therein, thereby retaining tension on the strap 12 when the windlass 16 has been wound so as to form a tourniquet on a person or animal.

As previously discussed, the gate member 30 is configured to receive and then retain either end portion 17' or 17" of the windlass 16 when an end of the windlass 16 is inserted between the arms 32 and 34 and the gate member 30 is forced in a downward direction until one end 17' or 17" of the windlass 16 passes the gate member 30 at which time the gate member 30 snaps back into engagement with the underside of the hook portion 32' of the arm 32. As will be described in more detail, to tighten the strap portion 18 around an extremity, the strap portion 18 is first wrapped around the extremity, the end 18" is passed through the slot 14" and pulled against the extremity to tighten the strap portion 18 around an extremity. The free end of the strap portion 18 extending from the slot 14" is then wrapped back upon itself so that the hook and loop surfaces of the strap portion 18 engage to hold the strap portion 18 around the extremity. This tightening action, however, is insufficient to provide proper tourniquet pressure to stop bleeding through an injured extremity. In order to further tighten the strap portion 18 around the extremity, the strap portion 20 is further tightened by winding the windlass 16 relative to the support structure 14. Winding of the windlass 16 causes the strap portion 20 to twist between the windlass 16 and the platform 40 of the securing structure 14. Once sufficiently tightened, by rotating the windlass, which may be one half a revolution, but more likely one or more times relative to the support structure 14, one end of the windlass 16 closest to the arms 32 and 34 can be inserted between the arms 32 and 34, past the gate 30 and retained by the gate 30 when the gate returns to biased engagement with the underside of the hook portion 32' so as to prevent the windlass 16 from disengaging from the support structure 14 in its tightened position. It is further contemplated that the gate 30 and arms 32 and 34 may be formed from a separate component rather than integrally formed with the platform 40 as shown and hingedly attached to the platform 40 so as to be foldable relative to the platform 40. This will allow the arms 32 and 34 and gate 30 to be pivoted 90 degrees from the platform 40 for a thinner profile when storing the tourniquet 10. In use, however, the arms 32 and 34 would automatically rotate to a vertical position relative to the platform 40 so that the windlass 16 could be retained thereby as discussed herein.

As previously discussed, the support structure 14 is comprised of a platform 40 that defines and extends between the slots 14' and 14". The arms 32 and 34 depend outwardly from the platform 40. The platform also includes a pair of opposing hollow cylinder mounts 42 and 44 that are attached to one side of the platform 40. The mounts 42 and 44 are spaced from one another and aligned such that the central longitudinal axis of each of the hollow cylinders of the mounts 42 and 44 are in alignment. The mounts 42 and 44 define cylindrical bores configured for receiving, and holding by friction fit, a cylindrically shaped translucent plastic tube containing isolated substances that, when combined, generate visible light through chemiluminescence, commonly known as a "glow stick" 46. The cylindrical bore of mount 44 passes completely through the mount 44. The cylindrical bore of mount 42, however, extends a distance into the mount 42 but does not pass completely therethrough. This allows an inserted end of the glow stick 46 to be inserted through the cylindrical bore of mount 44 and into the cylindrical bore of the mount 42 to be held therein between. The cylindrical bore of the mount 42 may be slightly inwardly tapered with the opening being wider than an inserted end of the glow stick 46 and becoming more narrowed along its depth so as to form a tight friction fit with the inserted end of the glow stick 46 when inserted into the mount 42. The glow stick 46 has a length sufficient to be at least partially held by each mount 42 and 44 when inserted into the mount 42. When inserted into the mounts 42 and 44, a central portion of the glow stick 46 is exposed in the window 48 defined by and between the mounts 42 and 44 and the platform 40. The platform 40, while being longitudinally and transversely rigid is formed to be thin enough to allow bending from front to back along its length. The platform 40 is also narrower in transverse width along the window 48. This further facilitates the ability of the platform 40 to curve or arch in a resilient manner from front to back as the strap 12 is tightened around an extremity. As the platform 40 curves around an extremity as the strap portions 18 and 20 are pulled relative to the slots 14' and 14", the glow stick 46 is also caused to be bent. That is, because the mounts 42 and 44 are each positioned proximate to the slots 14" and 14', respectively, the mounts 42 and 44 and their respective facing bores move from being longitudinally aligned, when the platform 40 is in a resting state, to being upwardly pointed in a direction away from the extremity as the platform 40 is arched. The arching movement of the platform 40 and corresponding movement of the mounts 42 and 44 relative to one another causes the plastic tube of the glow stick 46 to also bend or arch thereby causing the glass ampoule inside the glow stick 46 to break, releasing its chemical and causing the glow stick 46 to illuminate. As such, the tightening of the strap 12 around an appendage of a person or animal can automatically cause the glow stick 46 to illuminate when the tourniquet is applied. When illuminated, especially in dark or dim lighting conditions, a paramedic or other medical or emergency personnel can quickly visually notice that a tourniquet has been applied and can take any medical precautions needed. In situations when the tourniquet 10 is being applied to a larger extremity, such that the platform 40 may not bend a sufficient amount to cause the glow stick to illuminate, applying sufficient pressure to the glow stick 46 with a finger or thumb between the mounts 42 and 44 can cause the glow stick 46 to sufficiently bend to break the glass ampoule within the plastic tube and illuminate the glow stick 46. Once the glow stick 46 has been used to illuminate the tourniquet, it can be removed by sliding it from the mount 42 and through the open end 44' of the mount 44. It can then be replaced with a new glow stick for future use of the tourniquet 10. It should be noted that other luminescent systems, reflective materials, or devices may also be employed, such as, for example, a battery operated lighting system that is triggered when the tourniquet 10 is applied.

As discussed, to properly use the tourniquet 10, the strap 18 is placed around an appendage or extremity (e.g., arm, leg, finger, or paw) of a person or animal above the location (i.e., closer to the heart of the patient) of the bleeding injury. The free end 18" of the strap portion 18' is then threaded through the slot 14" of the support structure 14. The free end 18" is then tightly pulled and then attached back to itself such that the portion extending from the slot 14" is pressed against the portion wrapped around the extremity. The engagement of the mixed hook and loop material on these mating surfaces of the strap member 18 securely hold them together until the free end 18" is lifted to pull the two surfaces apart in order to remove the tourniquet 10. Once secure, the windlass 16 is rotated relative to the support structure 14 thereby causing the strap portion 20 adjacent the windlass 16 to be twisted between the windlass 16 and the support structure 14. The strap portion 20 adjacent the windlass 16 has an hourglass shape so as to be more narrow in width at the location 20 of the windlass 20. This narrowed portion of the of the strap portion 20 causes the windlass 18 to self-align relative to the strap portion 20 at the narrowed portion when winding of the windlass 18 begins thereby causing the windlass 18 to be approximately centrally positioned relative to the support structure 14 when rotated. Continued rotating of the windlass 16 effectively shortens the length of the strap portion 20 by bringing its ends 20' and 20" closer together and, in turn, further tightening the strap 18 around the extremity to which it is attached. The strap portion 20 adjacent to the windlass 16 is comprised of a thinner strap material (such nylon webbing alone without any hook and loop material) than the strap portion 18 (which also includes the thickness of the hook and loop material) to allow the strap portion 20 to be more easily twisted upon itself under the windlass 16 when wound. Once the windlass 16 has been rotated enough to sufficiently wind the strap portion 20 and to cause sufficient compression on the extremity so that bleeding from the injury has stopped, the end of the windlass 16 closest to the gate 30 in the direction of winding of the windlass 16 is inserted through the gate member 30 and held in place by the arms 32 and 43 and the gate 30 so that the windlass 16 cannot be removed from between the arms 32 and 43 and the gate 30 until the gate 30 is opened and the secured end of the windlass 16 is lifted from between the arms 32 and 34.

The ends 16' and 16" of the windlass 16 have a larger diameter than the adjacent end portions of the body of the windlass 16 to effectively form hooks or retention portions for engagement, i.e., abutment, with the outside of the arms 32 or 34 against which the windlass 16 is engaged. The position of the windlass 16 relative to the arms 32 and 34, the overall length of the windlass 16 and its widened ends 16' and 16" are configured to extend one end 16' or 16" of the windlass 16 outside of the arms 32 and 34 and gate 30 when the windlass 16 is rotated relative to the support structure 14 so as to cause one end 16' or 16" to be positioned between and outside the arms 32 and 34 (between about 45 to 135 degrees from its resting position as shown in FIGS. 1 and 2). Engagement of either end 16' or 16" of the windlass 16 with one of the arms 32 or 34 and/or the gate 30 when the windless 16 has been wound prevents the windlass 16 from being inadvertently dislodged from between the arms 32 and 34, thereby maintaining the pressure of the strap 18 on the extremity. In addition, the windlass 16 is provided with a plurality of texture features, such as circumferential protrusions and longitudinal recesses to increase the longitudinal strength and rigidity of the windlass 16 and to provide gripping points along the windlass when being grasped by a user. Both the support structure 14 and windlass 16 may be formed from plastic, as by injection molding, so as to decrease the overall weight of the tourniquet 10 but to provide sufficient structural integrity, functionality, and reliability of the tourniquet 10.

For those that are not familiarly with using the tourniquet 10 of the present invention and/or to record the time when the tourniquet 10 has been applied, the strap portion 22 is attached to the free end portion of the strap 18 on the side opposite the mixed hook and loop material. The strap portion 22 includes a label 22' that can include instructions for proper application and use of the tourniquet 10, a QR code that can be scanned to link to textual, graphical, or video instructions for use of the tourniquet 10 and/or to provide an area in which a time of application can be written. The strap portion 22 may also be made from a bright colored, fluorescent and/or light reflective strap material so as to make the tourniquet 10 more visible.

Figure 3:
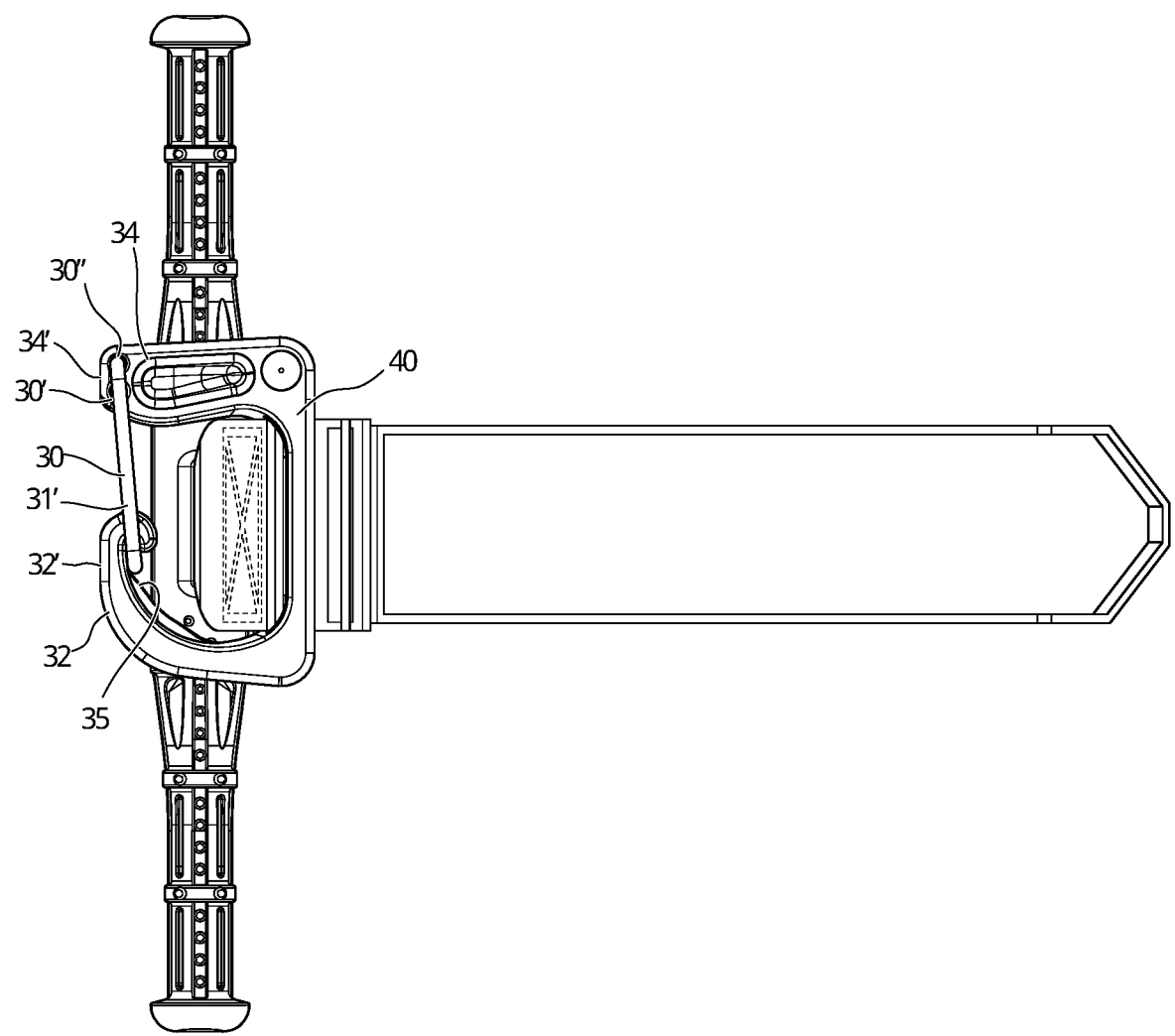
FIG. 3 is a front end view of the tourniquet shown in FIG. 1.

A shown in FIG. 3, the gate member 30 is self-biased between distal ends of arms 32 and 34 outwardly depending from the platform 40. The gate member 30 is comprised of a bent metal rod 31' outlining a generally rounded rectangular shape. The gate member 30 has first and second ends each pivotally attached to opposite sides of the distal end 34' of the arm 34 with the first and second ends horizontally offset from one another with the first end 30' positioned closer to the arm 32 and the second end 30" positioned farther from the arm 32 than the first end 30'. This offset arrangement creates a biasing force on the gate 30 to force the gate 30 into engagement with the underside 35 of the hook portion 32' of the arm 32. When the gate 30 is moved toward the platform 40 to allow passage of one end of the windlass 16, the gate 30 will automatically snap back against the hook portion 32' of the arm 32 so as to prevent the end of the windlass 16 from being dislodged form the gate 30.

The hook portion 32', also has a downwardly depending hook end so as to wrap around the gate 30 and thus further prevent the gate 30 from being pulled from the gate 30 even under force.

Figure 4:
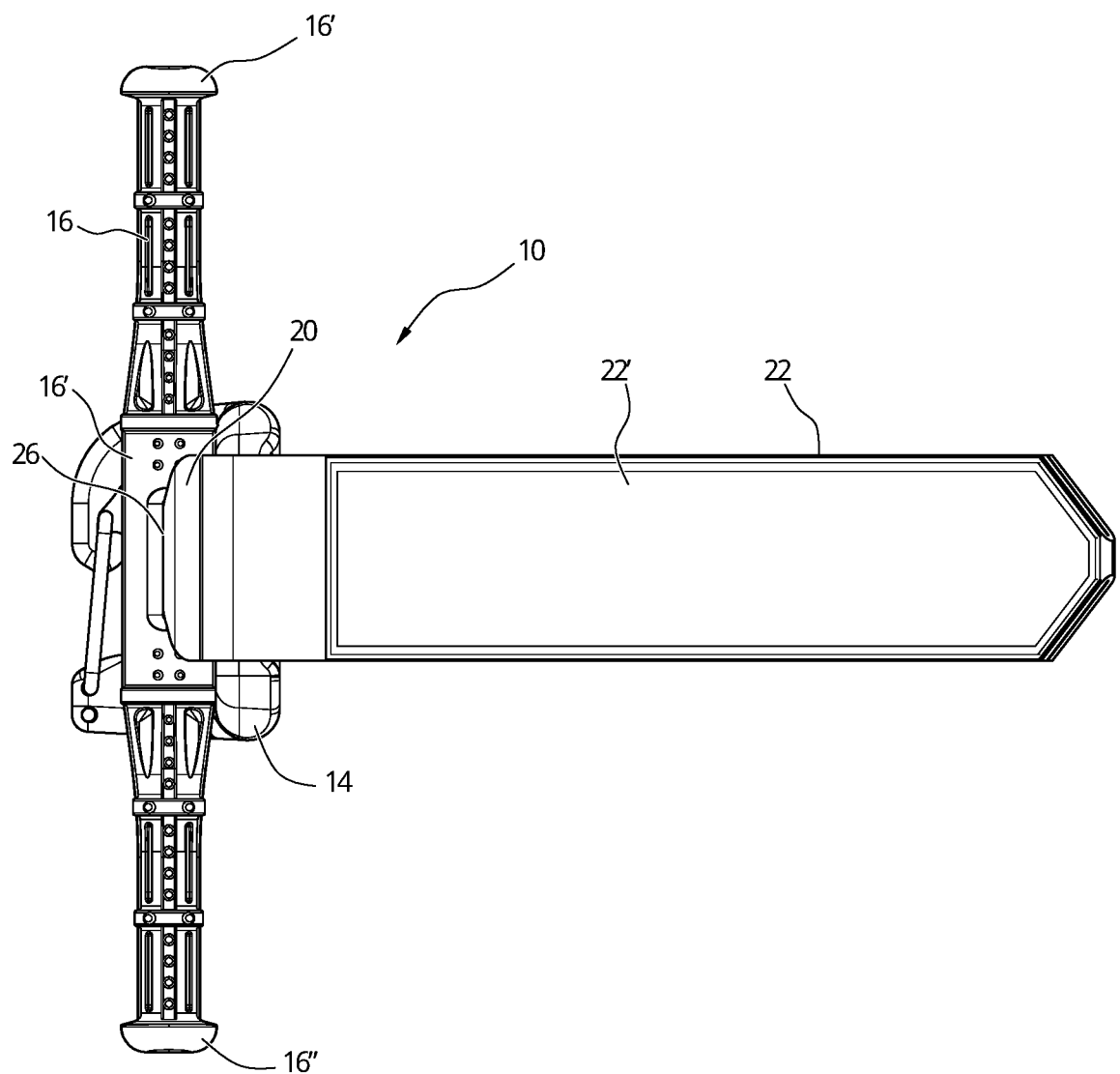
FIG. 4 is a back end view of the tourniquet shown in FIG. 1.

As shown in FIG. 4, the windlass 16 has a generally cylindrical shape with a wider central portion through which the slot 26 transversely extends for receiving the strap portion 20. The strap portion 20 at the slot 26 has an hourglass shape so as to narrow at the slot 26 with the width of the slot 26 being just slightly wider or approximately the same width as the width of the strap portion 20 at its most narrow width. The windlass 16 will thus tend to reside at this narrow portion of the strap portion 20 and thus be centered on the securing structure 14. The windlass 16 is tapered on either side from the central portion 16' and laterally extends therefrom a distance until terminated on each end by widened abutment ends 16' and 16" configured for being grasped by a user when winding the windlass and for engagement and retention with the outer sides of the gate arms 32 and 34 as previously described. The front side 22' of the strap 22 is configured to receive a label which may include various written or visual instructions for use of the tourniquet 10.

Figure 5:
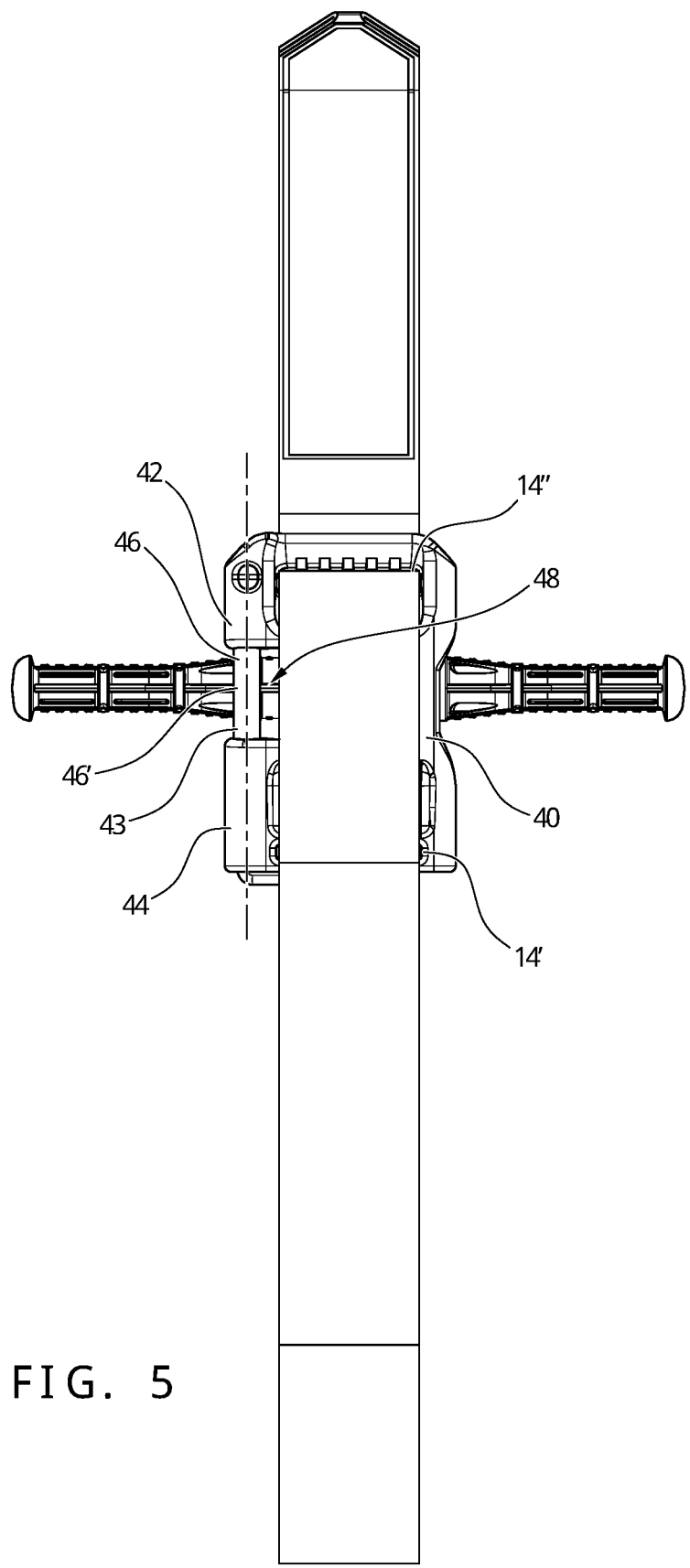
FIG. 5 is a bottom side view of the tourniquet shown in FIG. 1.

As shown in FIG. 5, the platform 40 includes a pair of opposing hollow cylinder mounts 42 and 44 that are attached to one side of the platform 40. As previously discussed, the mounts 42 and 44 are spaced from one another and aligned such that the central longitudinal axis of each of the hollow cylinders of the mounts 42 and 44 are in alignment. The mounts 42 and 44 define cylindrical bores configured for receiving, and holding by friction fit, a cylindrically shaped translucent plastic tube 43 containing isolated substances that, when combined, generate visible light through chemiluminescence, commonly known as a "glow stick" 46. The cylindrical bore of mount 44 passes completely through the mount 44. The cylindrical bore of mount 42, however, extends a distance into the mount 42 but does not pass completely therethrough. This allows an inserted end of the glow stick 46 to be inserted through the cylindrical bore of mount 44 and into the cylindrical bore of the mount 42 to be held therein between. The cylindrical bore of the mount 42 may be slightly inwardly tapered with the opening being wider than an inserted end of the glow stick 46 and becoming more narrowed along its depth so as to form a tight friction fit with the inserted end of the glow stick 46 when inserted into the mount 42 to prevent the glow stick 46 from falling out of the mount 42. The glow stick 46 has a length sufficient to be at least partially held by each mount 42 and 44 when inserted into the mount 42. When inserted into the mounts 42 and 44, a central portion 46' of the glow stick 46 is exposed in the window 48 defined by and between the mounts 42 and 44 and the platform 40. The platform 40, while being longitudinally and transversely rigid is formed to be thin enough to allow bending from front to back along its length. The platform 40 is also narrower in transverse width along the window 48. This further facilitates the ability of the platform 40 to curve or arch in a resilient manner from front to back as the strap 12 is tightened around an extremity. As the platform 40 curves around an extremity as the strap portions 18 and 20 are pulled relative to the slots 14' and 14", the glow stick 46 is also caused to be bent. That is, because the mounts 42 and 44 are each positioned proximate to the slots 14" and 14', respectively, the mounts 42 and 44 and their respective facing bores move from being longitudinally aligned, when the platform 40 is in a resting state, to being upwardly pointed in a direction away from the extremity as the platform 40 is arched. The arching movement of the platform 40 and corresponding movement of the mounts 42 and 44 relative to one another causes the plastic tube of the glow stick 46 to also bend or arch thereby causing the glass ampoule inside the glow stick 46 to break, releasing its chemical and causing the glow stick 46 to illuminate. As such, the tightening of the strap 12 around an appendage of a person or animal can automatically cause the glow stick 46 to illuminate when the tourniquet is applied. When illuminated, especially in dark or dim lighting conditions, a paramedic or other medical or emergency personnel can quickly visually notice that a tourniquet has been applied and can take any medical precautions needed.

Figure 6:
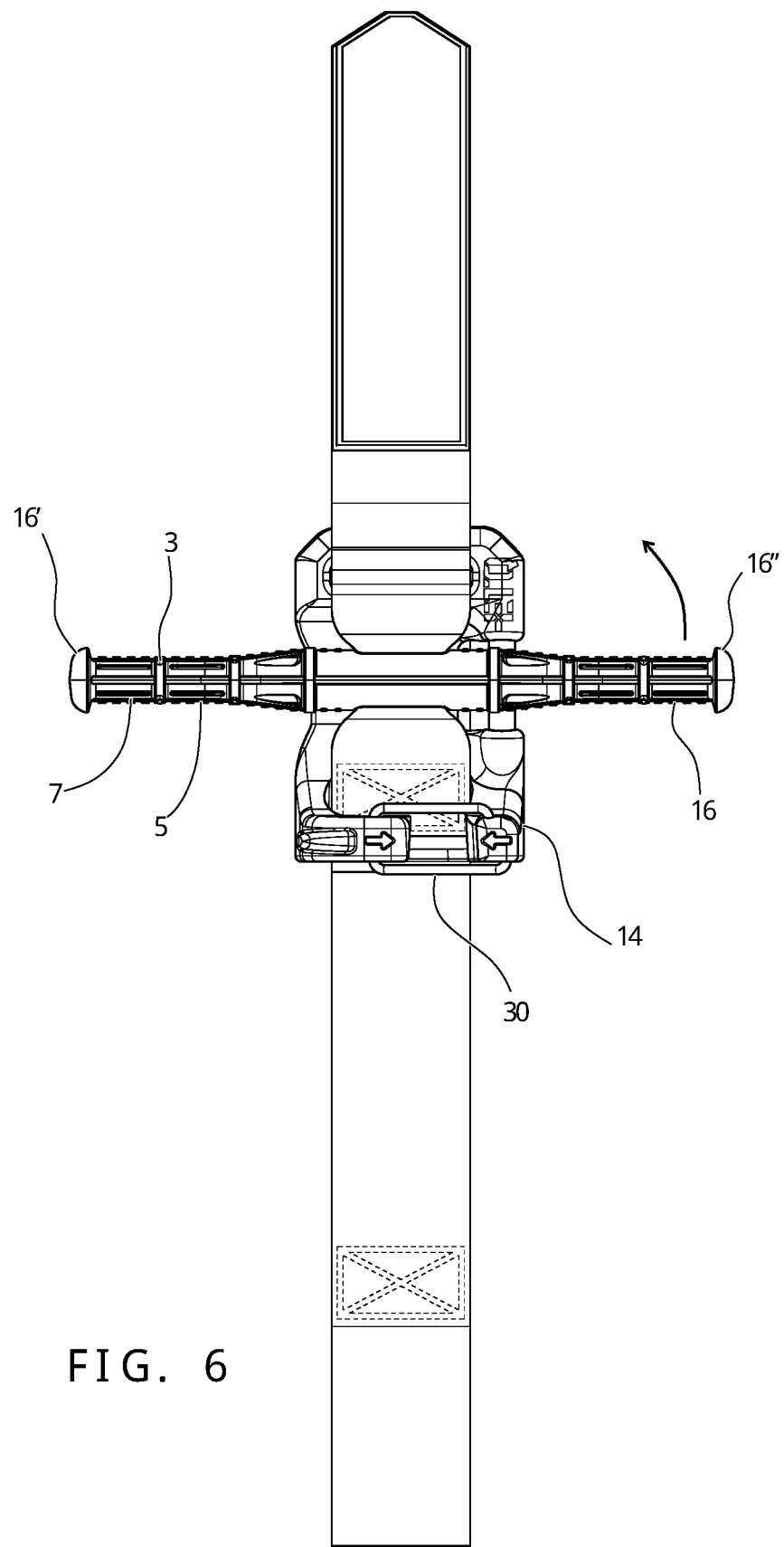
FIG. 6 is a top side view of the tourniquet shown in FIG. 1.

As shown in FIG. 6, the windlass 16 is provided with various texture features, such as circumferential ribs 3, protrusions or bumps 5, lateral ribs 7 and widened end caps 16' and 16". These features also provide structural strength to the windlass 16 while decreasing the weight of the windlass 16. The windlass 16 can be wound relative to the securing structure 14 as indicated by the arrow until one end 16' or 16" passes over the opening in the gate member 30 at which point the end adjacent the gate member 30 can be pressed through the gate member 30 until the gate member 30 snaps over the windlass to hold it between the arms 32 and 34 until released.

As previously discussed, the gate member 30 is configured to receive and then retain either end portion 17' or 17" of the windlass 16 when an end of the windlass 16 is inserted between the arms 32 and 34 and the gate member 30 is forced in a downward direction until one end 17' or 17" of the windlass 16 passes the gate member 30 at which time the gate member 30 snaps back into engagement with the underside of the hook portion 32' of the arm 32. As will be described in more detail, to tighten the strap portion 18 around an extremity, the strap portion 18 is first wrapped around the extremity, the end 18" is passed through the slot 14" and pulled against the extremity to tighten the strap portion 18 around an extremity. The free end of the strap portion 18 extending from the slot 14" is then wrapped back upon itself so that the hook and loop surfaces of the strap portion 18 engage to hold the strap portion 18 around the extremity. This tightening action, however, is insufficient to provide proper tourniquet pressure to stop bleeding through an injured extremity. In order to further tighten the strap portion 18 around the extremity, the strap portion 20 is further tightened by winding the windlass 16 relative to the support structure 14. Winding of the windlass 16 causes the strap portion 20 to twist between the windlass 16 and the platform 40 of the securing structure 14. Once sufficiently tightened, by rotating the windlass, which may be one half a revolution, but more likely one or more times relative to the support structure 14, one end of the windlass 16 closest to the arms 32 and 34 can be inserted between the arms 32 and 34, past the gate 30 and retained by the gate 30 when the gate returns to biased engagement with the underside of the hook portion 32' so as to prevent the windlass 16 from disengaging from the support structure 14 in its tightened position. It is further contemplated that the gate 30 and arms 32 and 34 may be formed from a separate component rather than integrally formed with the platform 40 as shown and hingedly attached to the platform 40 so as to be foldable relative to the platform 40. This will allow the arms 32 and 34 and gate 30 to be pivoted 90 degrees from the platform 40 for a thinner profile when storing the tourniquet 10. In use, however, the arms 32 and 34 would automatically rotate to a vertical position relative to the platform 40 so that the windlass 16 could be retained thereby as discussed herein.

Figure 7:
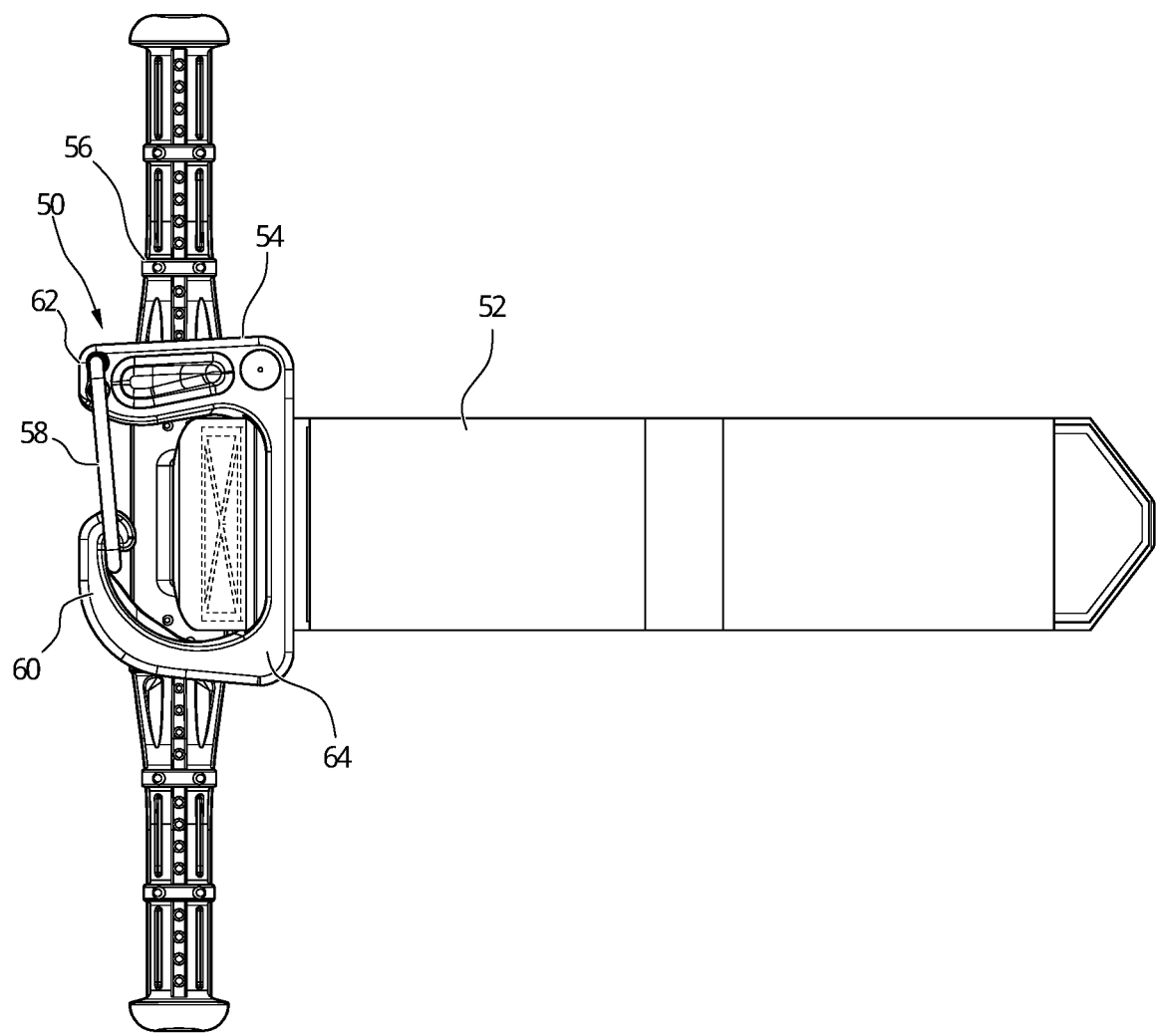
FIG. 7 is a front end view of a second embodiment of a tourniquet in accordance with the principals of the present invention.
Figure 8:
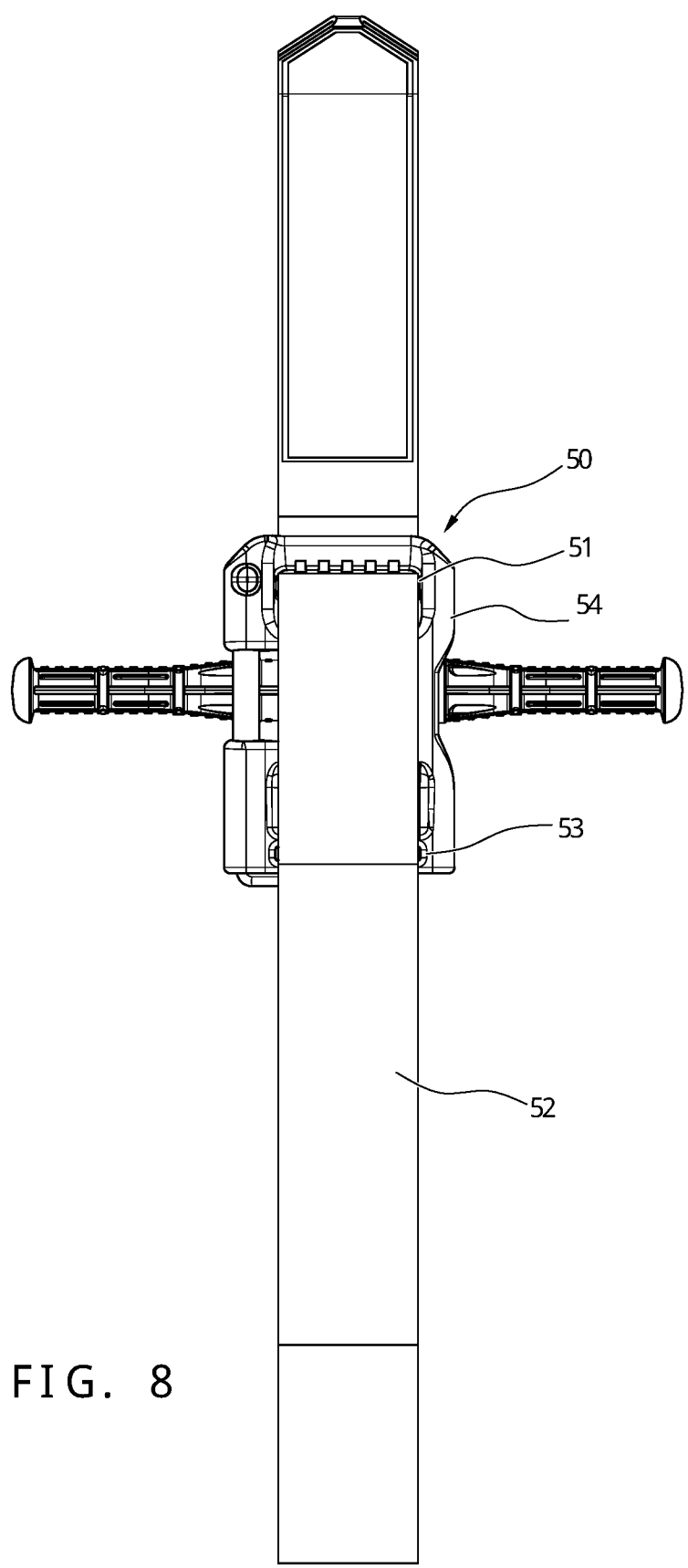
FIG. 8 is a bottom perspective view of the tourniquet shown in FIG. 7.

As shown in FIGS. 7 and 8, a tourniquet, generally indicated at 50, may be generally configured similar to the tourniquet 10 shown in FIG. 1, but configured to fit a wider strap 52. That is, the tourniquet 50 includes a support structure 54 having strap slots 51 and 53 through which the strap 52 can be threaded in a manner as previously described with reference to tourniquet 10 and a windlass 56 having a transverse slot 58 through which the narrow portion of the strap 52 is also threaded and resides. The width of the support structure 54 is made to be sider than the support structure 14 previously described herein to accommodate the wider strap 52. The support structure 54 also includes a biased gate 58 supported by arms 60 and 62 upwardly depending from the base 64 of the support structure 54, with the arm 60 forming a hook for catching and retaining the free end of the biased gate 58 on the underside thereof, which gate 58 can be opened by the windlass 56 when passed between the arms 60 and 62 until the gate 58 passes over the windlass 56 to hold and secure the windlass 56 between the arms 60 and 62 as the gate is biased back to the closed position as shown in FIG. 7.

Figure 9:
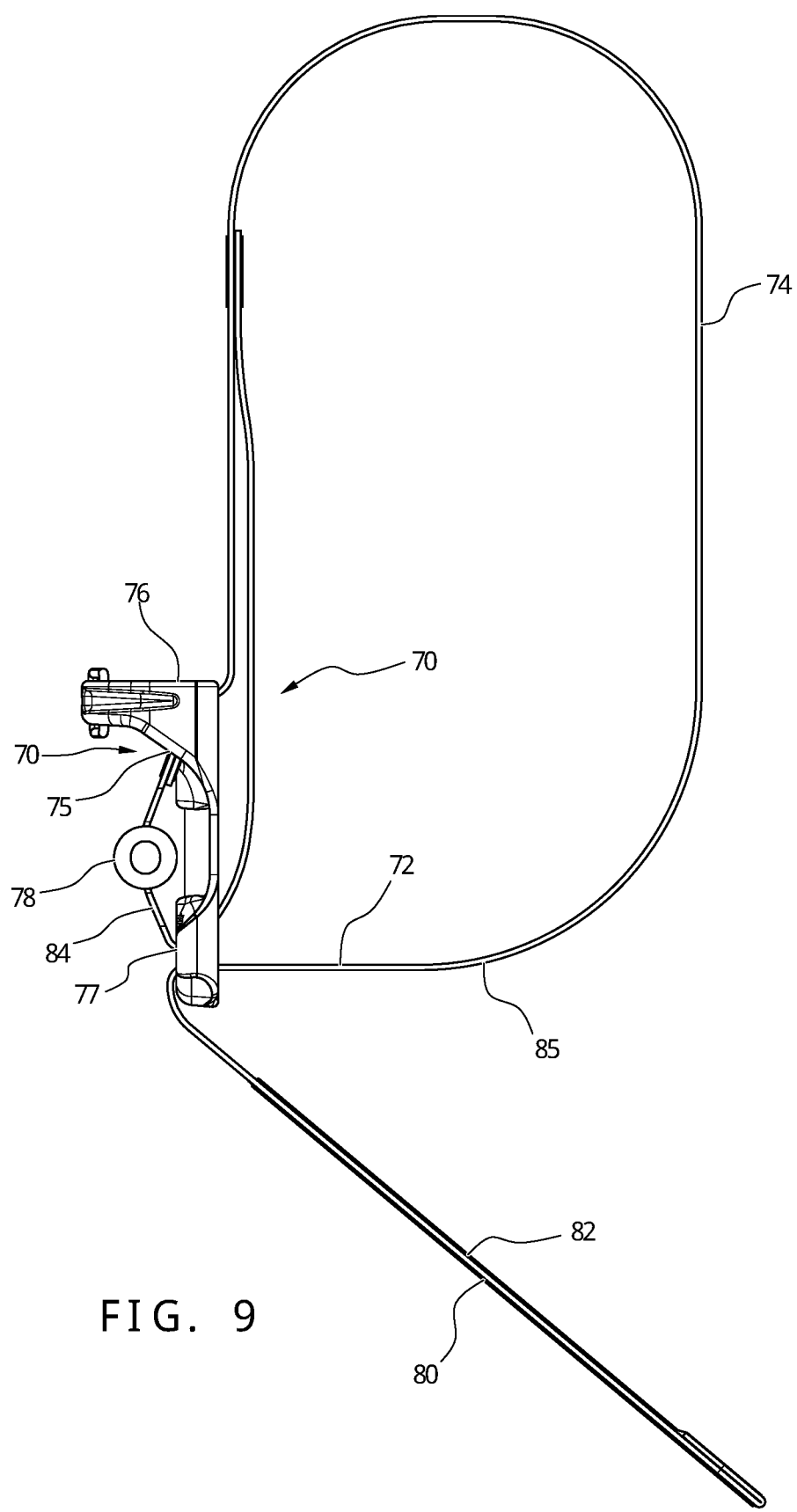
FIG. 9 is left side view of a third embodiment of a tourniquet in accordance with the principals of the present invention.
Figure 10:
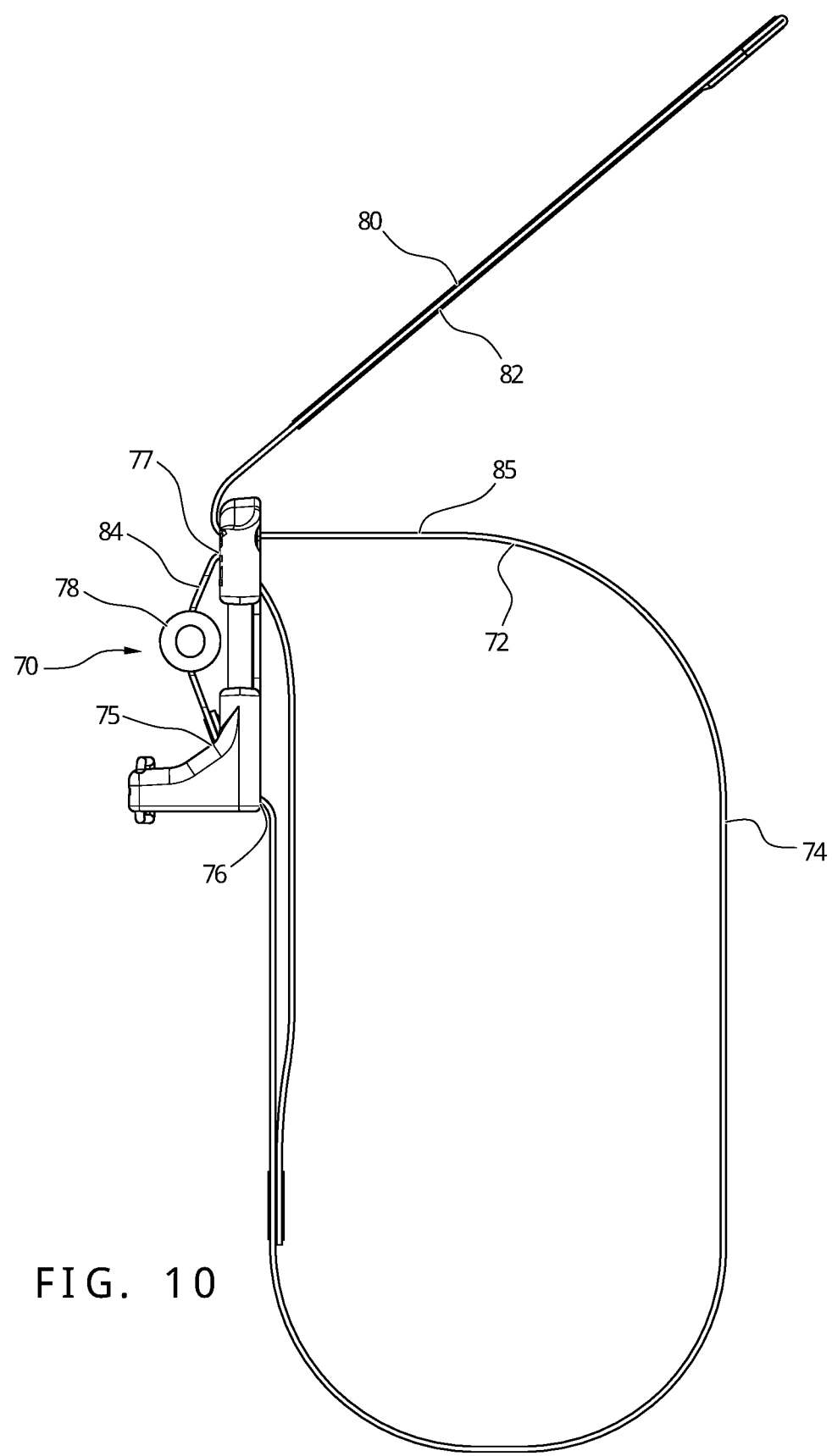
FIG. 10 is right side view of the tourniquet shown in FIG. 9.
Figure 11:
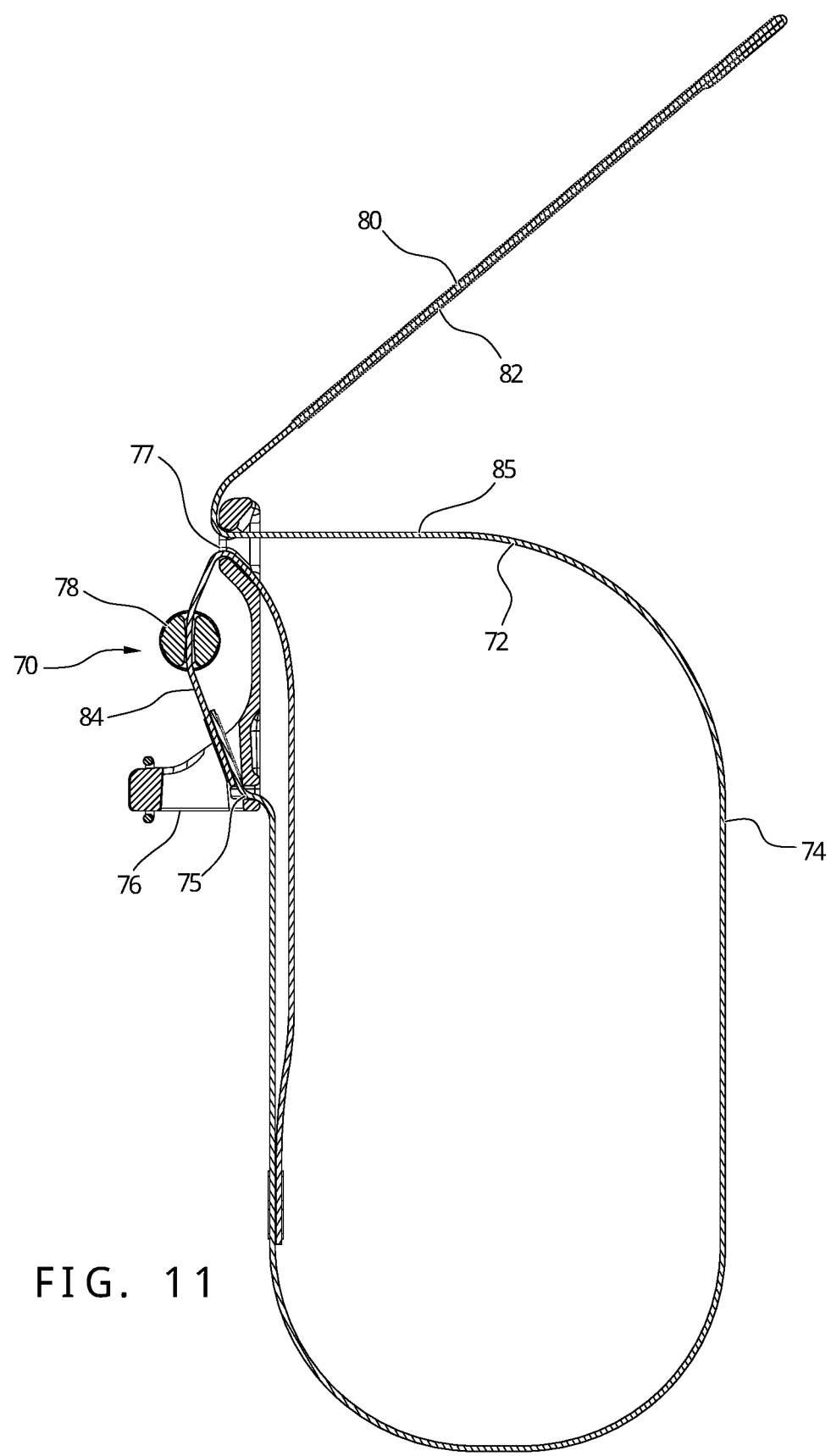
FIG. 11 is cross-sectional right side view of the tourniquet shown in FIG. 9.

As shown in FIGS. 9, 10 and 11, a strap 72 for a tourniquet 70 of the present invention may be formed from one or more sections of webbing material, such as nylon webbing that is not readily stretchable in its longitudinal or lengthwise direction. That is because, when applying a tourniquet in a manner of the present invention by tightening a strap around an appendage or extremity of a person or animal and then essentially locking that tensioned strap in place to hold pressure circumferentially around the appendage or extremity, if the material forming the strap were comprised of a material that could stretch along its length, the tension in the strap could relax, thus allowing blood to flow under the tourniquet. The strap 72 forms an elongated loop 74 at one end of the strap 72 that is threaded through a pair of slots 75 and 77 in the support structure 76 and the windlass 78 that is positioned between the slots 75 and 77. The free end 80 of the strap 72 is threaded through the slot 77 of the support structure and can be pulled against the support structure 76 to cause tension in the loop 74 that has been wrapped around an appendage or extremity. The underside 82 of the free end portion 80 of the strap 72 is provided with hook and/or loop material with the same side surface 85 of the loop 74 being provided with loop and/or hook material to mate with the hook and/or loop material of the free end portion 80 of the strap 72 when pressed against it. After the free end portion 80 has been secured to the loop portion 74 of the strap 72, the windlass 78 can be rotated relative to the support structure 76 so as to cause the strap portion 84 between the slots 75 and 77 to twist upon themselves thereby shortening the length of the loop 74 and tightening the loop 74 around the appendage or extremity.

Figure 12:
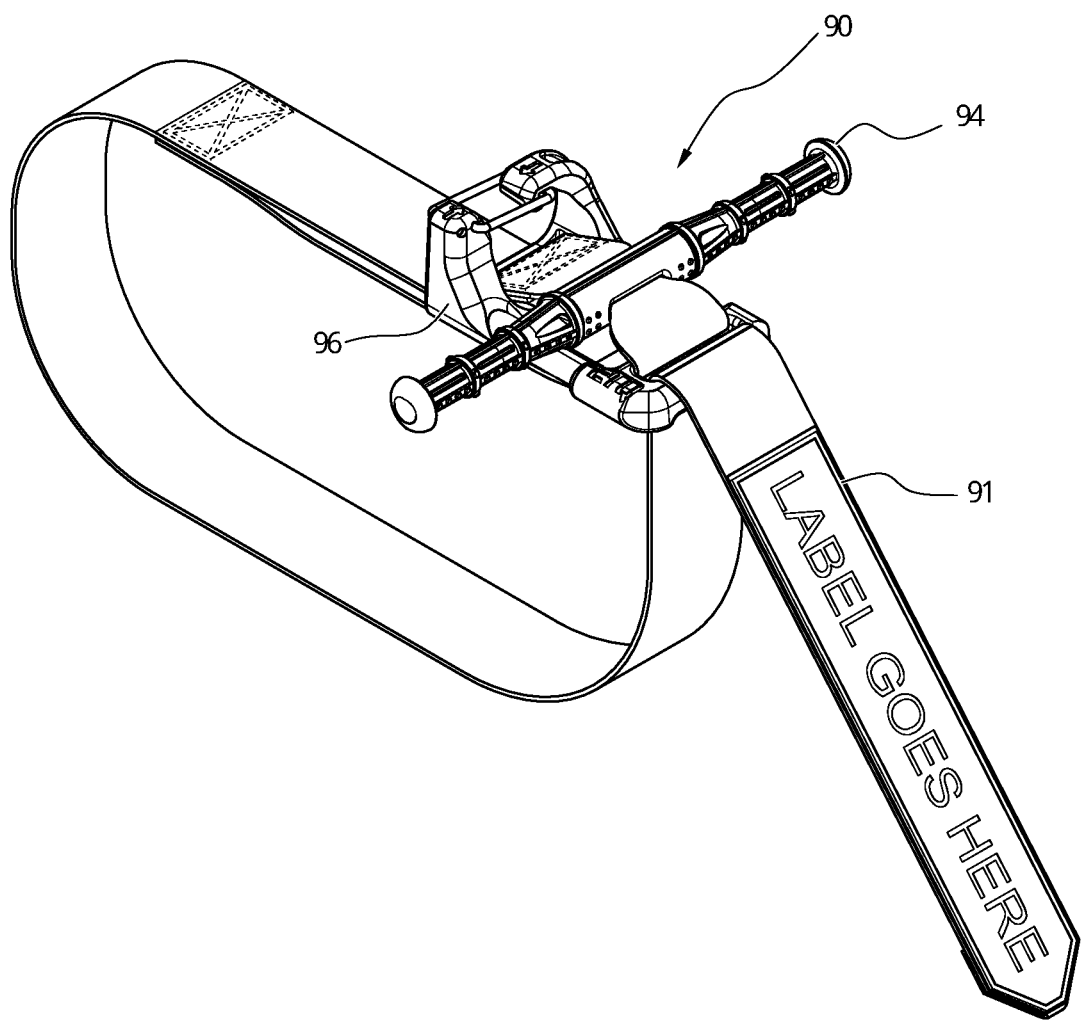
FIG. 12 is top perspective view of a fourth embodiment of a tourniquet in accordance with the principals of the present invention.
Figure 13:
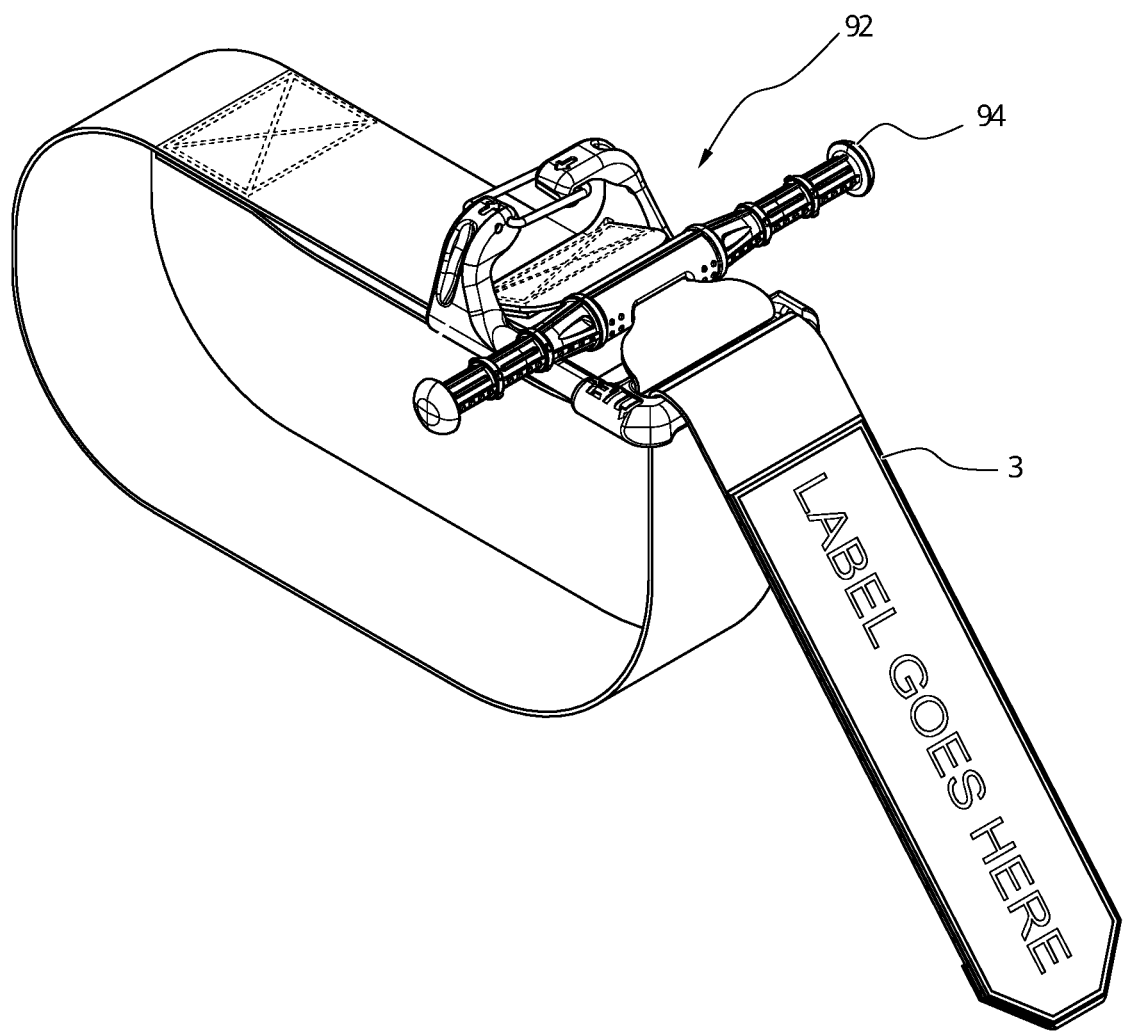
FIG. 13 is top perspective view of a fifth embodiment of a tourniquet in accordance with the principals of the present invention.

FIGS. 12 and 13 show comparative sizing of two different embodiments of a tourniquet 90 and 92 of different sizes to accommodate straps 91 and 93 of different widths, respectively. To do so, the same sized and configured windlass 94 may be used for both embodiments and only the width of the respective support structures 95 and 96 need be modified. That is, because the width of the strap is configured to be narrowed at the windlass 94, the straps 91 and 93 can each be narrowed to the same width at the location where the windlass 94 is to be attached to accommodate the same windlass 94 in each case. This saves manufacturing costs that would otherwise be incurred if a separate windlass needed to be created for each embodiment. While the strap 91 of FIG. 12 may be 1 inch or less in width, the strap 93 of the tourniquet in FIG. 12 is wider (e.g., 1.5 to 2 inches) for better blood occlusion and easier use, especially on larger extremities, and/or to meet military or other government or customer requirements.

As further illustrated in FIG. 12, the strap 91 may be formed from a single continuous strap that is sewn back upon itself to form the loop through and around the support structure 96 for placement around an extremity. Thus, a first end of the strap 91 is secured to the support structure 96 as by forming a loop as previously described that is sewn or otherwise permanently attached back upon itself after being threaded through the support structure 96. The free end of the strap 91 is then threaded through the opposite end of the support structure to form a larger loop for placement around an extremity of the patient.

Figure 14:
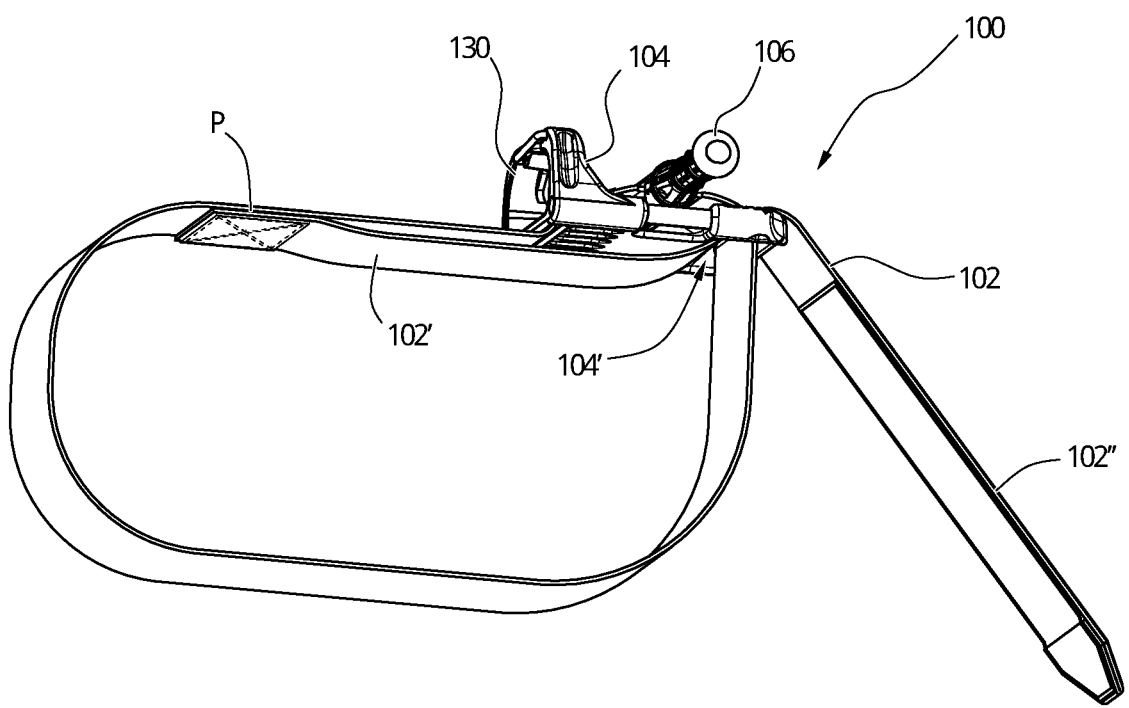
FIG. 14 is a side perspective view of sixth embodiment of a tourniquet in accordance with the principals of the present invention with a single strap slot in the support structure.

Referring to FIG. 14, there is shown yet another embodiment of a tourniquet 100 of the present invention. The tourniquet 100 is comprised of three structures or assemblies including a strap 102, a strap securing structure 104 and a tensioning device 106 in the form of a windlass. Like the strap 12 of FIG. 1. or the strap shown in FIG. 12, the strap 102 is comprised of a plurality of strap portions that may be formed from a single strap or separate strap sections that are sewn together or otherwise permanently attached to one another. The strap securing structure 104 is also similarly configured to the strap securing structure 14 of FIG. 1 but is provided with a single slot 104' at the end of the strap securing structure 104 opposite the gate 130. A first end 102' of the strap 102 extends through the gate 130, over the top surface of the securing structure 104, through the slot 104', back under the securing structure and fixedly attached to an underside of itself at a point P spaced from the securing structure 104 to form a loop with the securing structure 104 permanently attached to the strap 102. The windlass 106 in it unwound state as shown in FIG. 14 is oriented transversely to the strap member 102. The second end of the strap 102", which extends from proximate point P has a length that is sufficient to be wrapped around an extremity through the slot 104' and have wrapped back upon itself in an overlapping manner to attach to itself via the hook and loop fastener disposed on one side of the strap 102 as previously described with reference to the tourniquet 10 of FIG. 1. Thus, the tourniquet 100 of the present invention is configured with a single slot 104' in the support structure 104 but generally functions the same as the dual slot support structure 14 of tourniquet 10 previously shown and described herein.

The description and examples given above are merely illustrative and are not meant to be an exhaustive list of all possible embodiments, applications, or modifications of the invention. Thus, various modifications and variations of the described methods and systems of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in the medical sciences, orthopedic surgery, or related fields are intended to be within the scope of the appended claims.

The disclosures of all references and publications cited above are expressly incorporated by reference in their entireties to the same extent as if each were incorporated by reference individually.

What is claimed is:

1. A tourniquet, comprising:
a support structure having a platform defining a first strap slot proximate a first end of a back plate;

a first arm depending from a top surface of the back plate proximate a second end of the back plate and adjacent a first side of the back plate;

a second arm depending from the top surface of the back plate proximate the second end of the back plate, opposite the first arm and adjacent a second side of the back plate, the second arm forming a capture hook;

a gate member having a first end attached to a distal end of the first arm and a second end in biased engagement with an under side of the capture hook of the second arm;

a windlass defining a longitudinal slot extending therethrough; and a strap having a first strap portion having a length sufficient to extend around an extremity and extending from proximate the second end of the back plate and having a free end portion, the free end portion configured to be inserted through the first strap slot and pulled to tighten the strap around the extremity relative to the support structure, a second strap portion having a first end extending from the first strap portion proximate the second end of the back plate, the second strap portion extending over the platform, through the longitudinal slot of the windlass, through the first strap slot, and under the platform, the second strap portion having a second end fixedly attached to an underside of the first strap portion a distance from the second end of the back plate to form a loop;

whereby winding the windlass relative to the support structure causes the second strap portion to twist between the windlass and the support structure to effectively shorten the second strap portion to thereby tighten the first strap portion around an extremity to which the first strap portion is configured to be attached; and whereby one end of the windlass can be positioned between the first and second arms and retained by the gate member when the windlass has been wound relative to the support structure.

2. The tourniquet of claim 1, further comprising a glow stick removably attached to the back plate.

3. The tourniquet of claim 2, wherein the support structure includes a pair of mounting members positioned on one side of the platform for holding the glow stick relative to the support structure.

4. The tourniquet of claim 3, wherein the pair of mounting members are spaced apart to define a window for exposing a center portion of the glow stick to be visible.

5. The tourniquet of claim 4, wherein the back plate is bendable in a longitudinal direction when the strap is tightened around an extremity, which bending causes the pair of mounting members to arch thereby bending the glow stick to cause the glow stick to illuminate.

6. The tourniquet of claim 1, wherein the first and second strap portions comprise separate strap sections that are fixedly attached to one another.

7. The tourniquet of claim 1, wherein the first strap portion comprises a mixed hook and loop fastener on a first side thereof so as to be releasably attachable to itself when the free end portion of the first strap portion is threaded through the first strap slot and overlapped back upon the first strap portion.

8. The tourniquet of claim 1, wherein the gate member comprises a metal rod formed into a generally rounded rectangle with each end attached to an opposite side of the first arm in a horizontally offset arrangement and extending under the capture hook of the second arm, the gate member biased toward the capture hook.

9. The tourniquet of claim 7, further comprising a label attached to a second side of the free end portion of the first strap portion.

10. The tourniquet of claim 1, wherein the platform is thinner along its length between the first strap slot and the first and second arms than along a remainder of the platform to allow the platform to flexibly arch when applied to the extremity.

11. The tourniquet of claim 1, wherein the free end portion is configured to be inserted through the first strap slot and pulled to tighten the strap around the extremity relative to the support structure.

12. The tourniquet of claim 1, wherein the back plate further defines a second strap slot proximate the second end of the back plate and extending between the first and second arms, the second strap portion extending from the first strap portion, through the second strap slot, over the platform, through the longitudinal slot of the windlass and through the first strap slot.

* * * * *